(12) United States Patent
Zamyatin et al.

(10) Patent No.: US 10,575,795 B2
(45) Date of Patent: Mar. 3, 2020

(54) AUTOMATED PHASE SELECTION FOR ECG-GATED CARDIAC AXIAL CT SCANS

(71) Applicant: Analogic Corporation, Peabody, MA (US)

(72) Inventors: Alexander Zamyatin, Mayfield Heights, OH (US); Basak Ulker Karbeyaz, Concord, MA (US)

(73) Assignee: Analogic Corporation, Peabody, MA (US)

(*) Notice: Subject to any disclaimer, the term of this patent is extended or adjusted under 35 U.S.C. 154(b) by 0 days.

(21) Appl. No.: 16/310,714

(22) PCT Filed: Jan. 18, 2018

(86) PCT No.: PCT/US2018/014177
§ 371 (c)(1),
(2) Date: Dec. 17, 2018

(87) PCT Pub. No.: WO2019/143333
PCT Pub. Date: Jul. 25, 2019

(65) Prior Publication Data
US 2019/0374175 A1    Dec. 12, 2019

(51) Int. Cl.
*G06K 9/00*    (2006.01)
*A61B 6/03*    (2006.01)
(Continued)

(52) U.S. Cl.
CPC .............. *A61B 6/032* (2013.01); *A61B 6/486* (2013.01); *A61B 6/5264* (2013.01);
(Continued)

(58) Field of Classification Search
CPC ....... A61B 6/032; A61B 6/486; A61B 6/5264; A61B 6/5288; A61B 6/563; A61B 6/5211;
(Continued)

(56) References Cited

U.S. PATENT DOCUMENTS

2006/0133564 A1   6/2006 Langan et al.
2007/0076928 A1*  4/2007 Claus .................... G06T 11/006
                                                            382/128
(Continued)

OTHER PUBLICATIONS

International Written Opinion for International Application No. PCT/US2018/014177, dated Oct. 17, 2018, 6 pages.
(Continued)

*Primary Examiner* — Andrew M Moyer
(74) *Attorney, Agent, or Firm* — TraskBritt (57) ABSTRACT

Provided are one or more systems and/or techniques for mitigating motion artifacts in a computed tomography image of an anatomical object. Extended scan data is received and includes projections and backprojections acquired for parallel rays emitted by a radiation source at different angular locations within a first range of source angles. The projections and the backprojections are compared to identify differences between the projections and the backprojections at the different angular locations. Movement of the anatomical object during acquisition of the extended scan data at the different angular locations is quantified, and short scan data is identified. The short set includes a subset of the extended scan data acquired at different locations within a second range of source angles where the quantified movement of the anatomical object is less than a movement threshold. The computed tomography image of the anatomical object is reconstructed from the short scan data.

20 Claims, 6 Drawing Sheets

(51) Int. Cl.
    *A61B 6/00*    (2006.01)
    *G06T 11/00*   (2006.01)
    *G06T 7/00*    (2017.01)

(52) U.S. Cl.
    CPC ........... *G06T 11/005* (2013.01); *A61B 6/5211* (2013.01); *A61B 6/5288* (2013.01); *A61B 6/563* (2013.01); *G06T 7/0012* (2013.01); *G06T 11/008* (2013.01); *G06T 2207/10081* (2013.01); *G06T 2211/412* (2013.01)

(58) Field of Classification Search
    CPC ................. G06T 11/005; G06T 7/0012; G06T 2207/10081; G06T 11/008; G06T 2211/412
    USPC ................................................ 382/128–134
    See application file for complete search history.

(56)            References Cited

U.S. PATENT DOCUMENTS

2007/0217568 A1    9/2007    Edic
    2012/0215090 A1    8/2012    Pan et al.
    2016/0256127 A1    9/2016    Lee et al.

OTHER PUBLICATIONS

International Search Report for International Application No. PCT/US2018/014177, dated Oct. 17, 2018, 4 pages.

* cited by examiner

AUTOMATED PHASE SELECTION FOR ECG-GATED CARDIAC AXIAL CT SCANS

CROSS-REFERENCE TO RELATED APPLICATIONS

This application is a national phase entry under 35 U.S.C. § 371 of International Patent Application PCT/US2018/0141777, filed Jan. 18, 2018, designating the United States of America, which claims the benefit under Article 8 of the Patent Cooperation Treaty to U.S. Provisional Patent Application Ser. No. 62/618,216, filed Jan. 17, 2018, for "Optimal Cardiac Phase in Prospectively Gated Axial Cardiac CT Scans," the disclosure of each of which is hereby incorporated herein in its entirety by this reference.

TECHNICAL FIELD

The present application relates to the field of computed tomography (CT) and, more specifically, to image reconstruction systems and methods that at least partially eliminate motion artifacts from axially-aligned CT scans of a beating heart.

BACKGROUND

To improve temporal resolution in axial cardiac scans, short scans (e.g., half-scans, partial scans, etc.) are often used to obtain enough image data to allow a full representation of a segment of the heart to be reconstructed. Short scans involve taking x-ray measurements about a portion, but less than the entire circumference of the heart about an axis of rotation. Since short scans require less time to complete than full, 360° scans for a given scan speed, there is a greater likelihood of completing a short scan between heartbeats, a period when the heart is relatively stationary. A cross-sectional tomographic image, or "slice," of the heart is reconstructed from the data collected as a result of the x-ray measurements. However, heartrates naturally vary, even while a patient is resting. Because the duration of time between heartbeats is not constant, triggering a short scan so the short scan can be completed during a time when the heart is relatively stationary is difficult.

Modern CT scanners have the capability to capture x-ray data for single slices that are sixteen (16 cm) centimeters in axial length, which allows reconstruction of an image of the entire heart from a single short scan. But most cardiac CT scans continue to be performed with CT scanners that have a collimation requiring four individual slices, each four (4 cm) centimeters in axial length, to be assembled into an image of the entire heart. A portion of the data for one or more of the slices may be acquired during a time when motion of the heart during the cardiac cycle is most pronounced. The use of data acquired during the pronounced motion of the heart results in distortions to the resulting tomographic image referred to as motion artifacts. Motion artifacts appearing in one or more of the slices to be assembled into the image of the entire heart diminish the quality of the assembled image.

BRIEF SUMMARY

Aspects of the present application address the above matters, and possibly others. According to one aspect a method of mitigating motion artifacts in a computed tomography image of an anatomical object is provided. The method includes receiving, at an image reconstructor, extended scan data comprising projections and backprojections acquired for parallel rays emitted by a radiation source at different angular locations within a first range of source angles. The first range of source angles extends greater than 240° about an axis of rotation of the radiation source. The projections and the backprojections are compared to identify differences between the projections and the backprojections at the different angular locations. Based on the identified differences between the projections and the backprojections, movement of the anatomical object during acquisition of the extended scan data at the different angular locations is quantified. Short scan data comprising a subset of the extended scan data acquired at different locations within a second range of source angles where the quantified movement of the anatomical object is less than a movement threshold is identified. The second range of source angles is less than the first range of source angles about the axis of rotation. The computed tomography image of the anatomical object is reconstructed from the short scan data.

According to another aspect, a computed tomography system is provided. The computed tomography system includes a radiation source, a detector array, and an image reconstructor. The image reconstructor is configured to receive extended scan data comprising projections and backprojections acquired for parallel rays emitted by the radiation source at different angular locations within a first range of source angles. The first range of source angles extends greater than 240° about an axis of rotation of the radiation source. The image reconstructor is configured to compare the projections and the backprojections to identify differences between the projections and the backprojections at the different angular locations. Based on the identified differences between the projections and the backprojections, the image reconstructor quantifies movement of the anatomical object during acquisition of the extended scan data at the different angular locations. The image reconstructor is configured to identify short scan data comprising a subset of the extended scan data acquired at different locations within a second range of source angles where the quantified movement of the anatomical object is less than a movement threshold. The second range of source angles is less than the first range of source angles about the axis of rotation. The image reconstructor is also configured to reconstruct the computed tomography image of the anatomical object from the short scan data.

According to another aspect, a non-transitory computer readable medium comprising computer executable instructions that when executed via a processing unit cause performance of operations, is provided. The operations involve extended scan data comprising projections and backprojections acquired for parallel rays emitted by a radiation source at different angular locations within a first range of source angles. The first range of source angles extends greater than 240° about an axis of rotation of the radiation source. The operations include comparing the projections and the backprojections to identify differences between the projections and the backprojections at the different angular locations. Based on the identified differences between the projections and the backprojections, movement of the anatomical object during acquisition of the extended scan data at the different angular locations is quantified. Short scan data is identified, and includes a subset of the extended scan data acquired at different locations within a second range of source angles where the quantified movement of the anatomical object is less than a movement threshold. The second range of source angles is less than the first range of source angles about the axis of rotation of the radiation source. The computed tomography image of the anatomical object is reconstructed from the short scan data.

Those of ordinary skill in the art may appreciate still other aspects of the present application upon reading and understanding the appended description.

BRIEF DESCRIPTION OF THE DRAWINGS

The application is illustrated by way of example and not limitation in the figures of the accompanying drawings, in which like references generally indicate similar elements and in which.

DETAILED DESCRIPTION

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

Among other things, one or more systems and/or techniques for mitigating motion artifacts in a computed tomography image of an anatomical object are provided herein. Anatomical objects such as a beating heart, for example, necessarily move when functioning properly. Movements of the heart during a heartbeat may seem to occur according to a fixed periodical schedule, but the timing of such movements actually varies. Each scan forming a slice of the heart image involves the collection of extended scan data during an anticipated phase of a cardiac cycle, with the x-ray, or other radiation source at different angular locations within a first range of source angles. The first range of source angles can cover one, or less than one full rotation about an axis of rotation.

The first range of source angles is greater than at least a minimum, second range of source angles required for reconstruction of an image from the short scan. Because the scan data is collected over the first range of source angles at more angular locations about the axis of rotation than required to reconstruct the image, acquired scan data at a portion of those angular locations can be omitted from the reconstruction. Thus, the second range of angles corresponding to the short scan data from which the three-dimensional computed tomography image is to be reconstructed can be selected anywhere within the first range of source angels to mitigate motion artifacts in the reconstructed image.

Utilizing computational resources to reconstruct the three-dimensional images from the short scan data so a user can manually select the image with the least noise is computationally inefficient, and time consuming. Instead, the second range of source angles for the short scan data can be identified utilizing data in the two-dimensional sinogram space. Identification of the second range of source angles can be performed before the computed tomography image is generated. The computed tomography image can then be reconstructed from the short scan data acquired at the identified second range of source angles. The three-dimensional computed tomography image reconstructed based on the short scan data can optionally be reconstructed exclusively of the extended scan data that was captured at angular locations that are outside of the second range of source angles.

Accordingly, as provided herein, selection of a subset of extended scan data to be used for reconstruction of a computed tomography image is improved so that motion artifacts are mitigated. In particular, a projection and backprojection for parallel rays of radiation emitted at each of a plurality of angular orientations about an axis of rotation are obtained. The projections and backprojections are compared to identify differences between each projection and backprojection of x-ray radiation at those different angular locations about an axis of rotation. The projections and the backprojections constitute two-dimensional data acquired using parallel rays of radiation as part of the scan. Based on the identified differences, movement of the anatomical object during acquisition of the extended scan data at the different angular locations is quantified. Short scan data is identified as including a subset of the extended scan data acquired at different locations within a second range of source angles where the quantified movement of the anatomical object is less than a movement threshold. Identification of the short scan data can optionally occur before the computed tomography image is generated based on the extended data set. The computed tomography image of the anatomical object is reconstructed from the short scan data. Thus, the presence of motion artifacts in the computed tomography image resulting from movement of the anatomical object during acquisition of the scan data can be efficiently mitigated.

Figure 1:
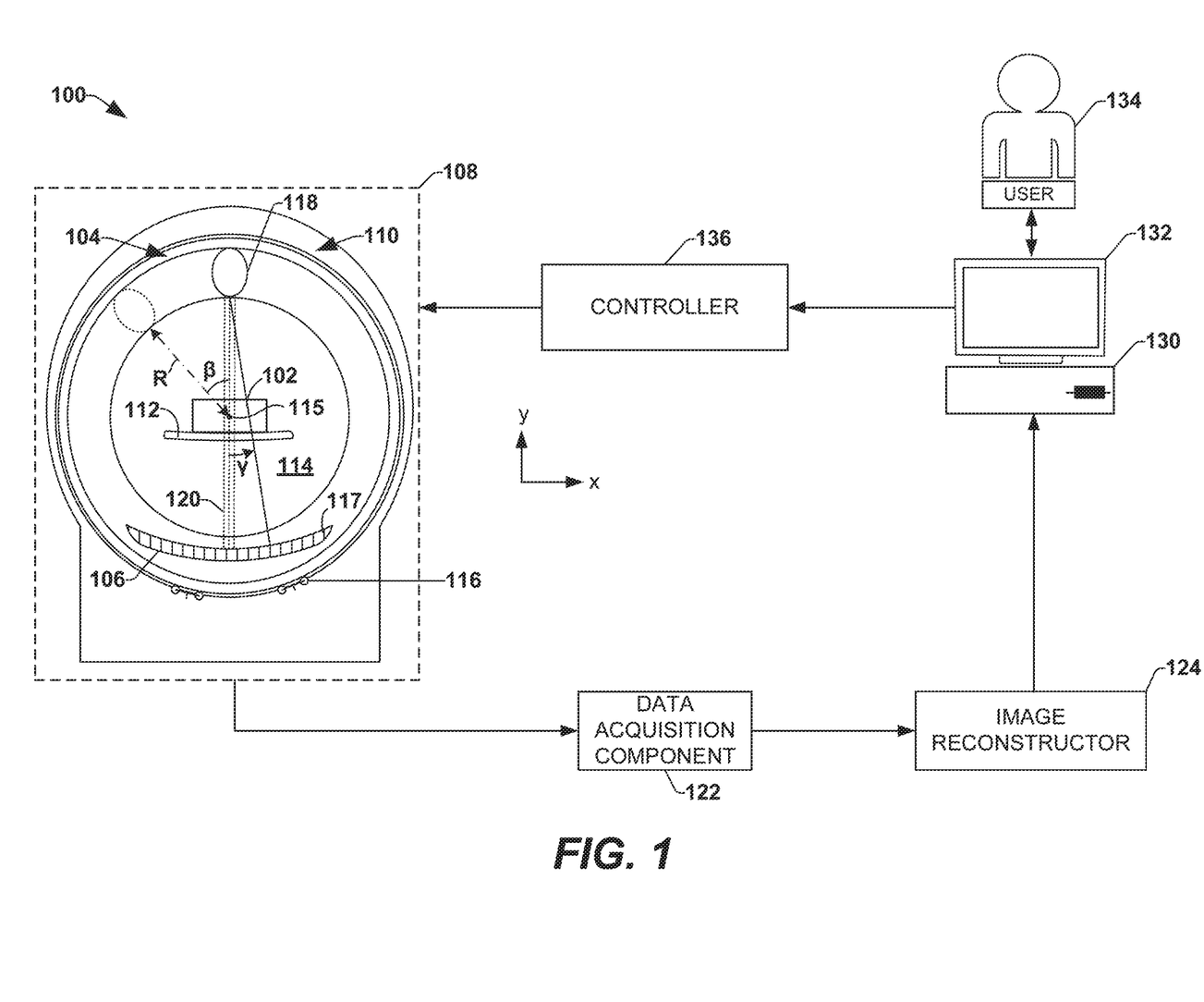
FIG. 1 illustrates an example environment of a computed tomography imaging modality.

FIG. 1 is an illustration of an illustrative environment 100 comprising a computed tomography (CT) system that may be configured to generate computed tomography images representative of an anatomical object 102 (e.g., patient, organ, muscle, tissue, etc.) or aspect(s) thereof. Such a system may be employed for mitigating motion artifacts that would otherwise appear in the computed tomography images as a result of movement of the anatomical object 102 during scanning.

It may be appreciated that while the environment 100 in FIG. 1 describes a CT system configured to generate two-dimensional and/or three-dimensional images of the anatomical object 102 under examination, other radiation imaging modalities are also contemplated for generating images of the anatomical object 102, optionally for diagnostics purposes. Moreover, the arrangement of components and/or the types of components included in the environment 100 are merely provided as an example. By way of example, in some embodiments, a data acquisition component 122 is comprised within a detector array 106.

Figure 2A:
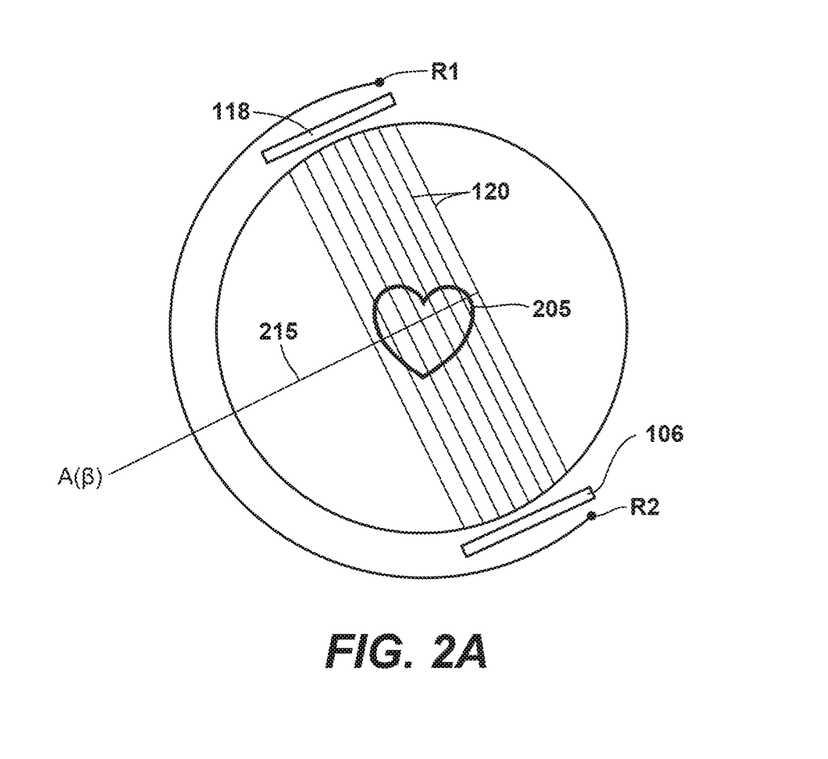
FIG. 2A is a schematic representation of parallel ray emissions at different angular locations within a range of source angles.
Figure 2B:
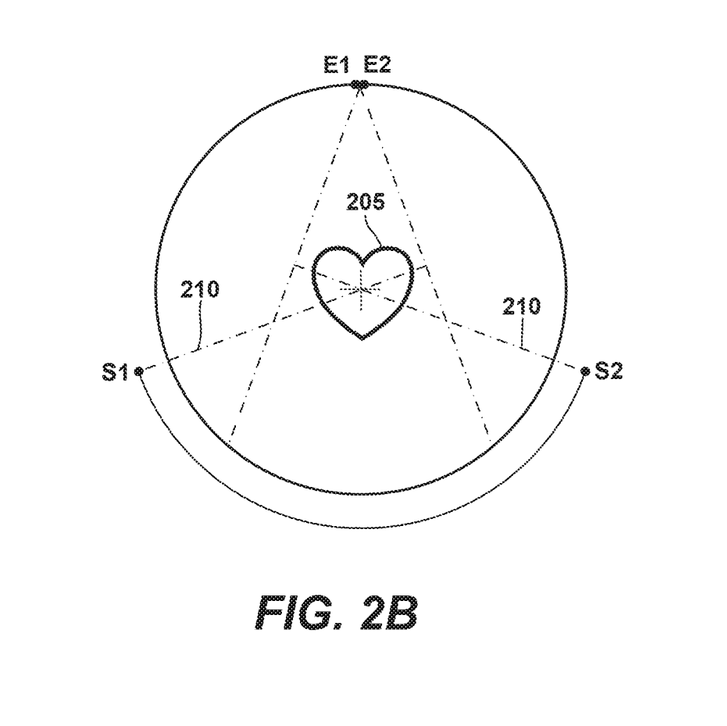
FIG. 2B is a schematic representation the acquisition of extended scan data and an identified range of view angles for short scan data.

In the embodiment of the environment 100 in FIG. 1, an examination apparatus 108 of the CT system is configured to examine one or more anatomical objects 102, including an anatomical object prone to movement, such as the heart 205 shown schematically in FIGS. 2A and 2B. With continued reference to FIG. 1, the examination apparatus 108 can comprise a rotating gantry 104 and a (stationary) support structure 110 (e.g., which may encase and/or surround at least a portion of the rotating gantry 104 (e.g., as illustrated with an outer, stationary ring, surrounding an outside edge of an inner, rotating ring)). During an examination of the anatomical object 102, the anatomical object 102 can be placed on a support article 112, such as a bed or conveyor belt, for example, that is selectively positioned in an examination region 114 (e.g., a hollow bore in the rotating gantry 104), and the rotating gantry 104 can be rotated and/or supported about an axis of rotation 115, and about the anatomical object 102 by a rotator 116, such as a motor, drive shaft, chain, roller truck, etc.

The axis of rotation 115 for a cylindrical CT system may be located at the center of the examination region 114, which is also the isocenter of the examination apparatus 108. The isocenter is the space through which the central ray of a set of beams of radiation 120 passes, and the anatomical object 102 may be positioned within the examination region 114 so the region of interest (the heart in the examples below) is centered at, or located adjacent to the isocenter. The distance R from the radiation source(s) 118 to isocenter is represented in broken lines in FIG. 1.

The rotating gantry 104 may surround a portion of the examination region 114 and may comprise one or more radiation sources 118 (e.g., an ionizing x-ray source, gamma radiation source, etc.) and a detector array 106 that is mounted on a substantially diametrically opposite side of the rotating gantry 104 relative to the radiation source(s) 118. The rotating gantry 104 can be rotated to sweep the radiation source(s) 118 through the plurality of angular locations about the axis of rotation 115, making full 360° revolutions. The angle $\beta$ in FIG. 1 generally represents the gantry angle or the source angle at the different angular locations of the views as described below. During an examination of the anatomical object 102, the radiation source(s) 118 emits fan, cone, wedge, parallel beam (shown in the drawings), and/or other shaped radiation 120 configurations from a focal spot(s) of the radiation source(s) 118 (e.g., a region within the radiation source(s) 118 from which radiation 120 emanates) into the examination region 114. It may be appreciated that such radiation 120 may be emitted substantially continuously and/or may be emitted intermittently (e.g., a brief pulse of radiation is emitted followed by a resting period during which the radiation source(s) 118 is not activated).

As the emitted radiation 120 traverses the anatomical object 102, the radiation 120 may be attenuated differently by different aspects of the anatomical object 102. Because different aspects attenuate different percentages of the radiation 120, an image(s) may be generated based upon the attenuation, or variations in the number of photons that are detected by the detector array 106. For example, more dense aspects of the anatomical object 102, such as a bone, a metal plate, electronic components, etc., may attenuate more of the radiation 120 (e.g., causing fewer photons to strike the detector array 106) than less dense aspects, such as skin or clothing.

The detector array 106 is configured to directly convert (e.g., using amorphous selenium and/or other direct conversion materials) and/or indirectly convert (e.g., using photodetectors and/or other indirect conversion materials) detected radiation into signals that can be transmitted from the detector array 106 to the data acquisition component 122 configured to compile signals that were transmitted within a predetermined time interval, or measurement interval, using various techniques (e.g., integration, photon counting, etc.). It may be appreciated that such a measurement interval may be referred to as a "view" and generally reflects signals generated from radiation 120 that was emitted while the radiation source(s) 118 was at a particular angular location relative to the anatomical object 102. Based upon the compiled signals, the data acquisition component 122 can generate projection data indicative of the compiled signals, for example.

The detector array 106 may be divided into a plurality of detector cells 117 arranged in rows and columns. Using the XYZ coordinates of FIG. 1 as a reference, the detector cells may be arranged in rows that extend in the X direction, and columns that extend in the Z direction, which is a direction parallel with the axis of rotation 115. The fan angles $\gamma$ in FIG. 1 are the individual angle of each detector cell 117, as seen from the radiation source(s) 118, or the angle relative to the center ray emitted by the radiation source(s) 118. As discussed in detail below, midplane projection and backprojection data may be collected and used to compare the projections with the backprojections. Midplane data includes only projection and backprojection data acquired by a centrally located portion of the rows of the detector array 106.

For example, an embodiment of the CT system using forty (40 mm) millimeter (or four (4 cm) centimeter) collimation includes sixty four (64) rows of detector cells to capture each of four slices that are to be assembled into a single three-dimensional image encompassing the entire heart 205. A set of parallel x-ray beams, referred to herein as parallel rays of radiation 120, shown in FIGS. 1 and 2A, emitted by the radiation source(s) 118 encounter the anatomical object 102 before being received by the detector array 106. The midplane data comprises projection and backprojection data collected by one, or a plurality of centrally-located rows which, in the present example of sixty four (64) rows (numbered sequentially), includes the $32^{nd}$ and $33^{rd}$ rows. The centrally-located rows are used to collect the midplane data for comparing the projections and backprojections because the projections and backprojections of the centrally-located rows are substantially aligned with each other. For a stationary anatomical object 102, there is little to no offset between the projections and corresponding backprojections caused by the position of the midplane detector cells relative to the radiation source(s) 118, referred to as the cone angle, for example. Thus, any differences or mismatches between the projections and backprojections detected by the detector cells in the centrally-located rows is attributed to movement of the anatomical object 102 during acquisition of the projection and backprojection data.

The illustrative example of the environment 100 further comprises an image reconstructor 124 configured to receive the projection and backprojection data that is output by the data acquisition component 122. The image reconstructor 124 is configured to generate three-dimensional image data (also referred to as three-dimensional image(s)) of the anatomical object 102 from the projection data using a suitable analytical, iterative, and/or other reconstruction technique (e.g., back projection reconstruction, tomosynthesis reconstruction, iterative reconstruction, etc.). In this way, the data is converted from the two-dimensional projection, or sinogram space to a three-dimensional image space of the computed tomography images, a domain that may be more understandable by a user 134 viewing the image(s), for example.

The illustrative environment 100 further comprises a terminal 130, or workstation (e.g., a computer), that may be configured to receive the image data (e.g., output by the image reconstructor 124). The terminal 130 may also be configured to present the image data and/or information for display on a monitor 132 to the user 134 (e.g., medical personnel, etc.). In this way, the user 134 can inspect the image(s) to identify areas of interest within the anatomical object 102, possibly for diagnostic purposes. The terminal 130 can also be configured to receive user input, which can direct operations of the examination apparatus 108 (e.g., a speed of a conveyor belt), for example.

In the illustrated embodiment environment 100, a controller 136 is operably coupled to the terminal 130. In one example, the controller 136 is configured to receive input from the terminal 130, such as user input for example, and to generate instructions for the examination apparatus 108 indicative of operations to be performed. For example, the user 134 may desire to reexamine the anatomical object 102, and the controller 136 may issue a command instructing the support article 112 to reverse direction (e.g., bringing the anatomical object 102 back into an examination region 114 of the examination apparatus 108).

It may be appreciated that the component diagram of FIG. 1 is merely intended to illustrate one embodiment of one type of imaging modality and is not intended to be interpreted in a limiting manner. For example, the functions of one or more components described herein may be separated into a plurality of components and/or the functions of two or more components described herein may be consolidated into merely a single component. Moreover, the imaging modality may comprise additional components configured to perform additional features, functions, etc., and/or some components described herein may be optional.

Extended scan data is acquired over a first range of source angles that can extend greater than 240° about the axis of rotation 115, such as at least 270° about the axis of rotation 115, or a full 360° about the axis of rotation 115, for example. Short scan data to be used to reconstruct the computed tomography image is identified by the image reconstructor 124 to include a subset, but less than all of the extended scan data. For example, the short scan data includes a portion of the extended scan data that is acquired with the radiation source(s) 118 at various angular locations within a second range of source angles. The second range of source angles constitutes a continuous block of, but less than all of the first range of source angles about the axis of rotation 115. For example, the second range of source angles can be chosen to include any block of at least 200°, at least 205°, at least 210°, at least 215°, at least 220°, at least 225°, at least 230°, or at least 240° of the first range of source angles corresponding to the extended scan data. The second range of source angles corresponds to the short scan data including the projection and backprojection data acquired with the radiation source(s) 118 at locations where the movement of the heart 205 is less than a movement threshold, described below (e.g., while the heart 205 is relatively stationary). For example, the heart 205 is relatively stationary during the diastole or mid-diastole period as opposed to during the QRS complex of the cardiac cycle.

For the sake of clarity and brevity, specific examples of a system and method for reconstructing a computed tomography image are described below. However, it is to be understood that the present disclosure is not limited to the specific numerical values utilized in the examples. Instead, the general concepts described herein are equally applicable for use with different operational parameters.

In the examples below, the anatomical object 102 is a beating heart 205, and the modality is a CT scanner that acquires projection and backprojection data based on parallel x-ray radiation emitted by the radiation source(s) 118 at various different angular locations about the axis of rotation 115. The first range of source angles extends a full 360° about the axis of rotation 115 and the second range of source angles includes a portion of the first range of source angles that extends 225° about the axis of rotation 115. The extended scan data will include projection and backprojection data acquired at nine hundred sixty (960) views of the heart 205 over the full (e.g., 360°) rotation about the axis of rotation 115. Thus, for each half of a full 360° scan about the axis of rotation 115, there are four hundred eighty (480) views. A computed tomography image is to be reconstructed from the data acquired from six hundred (600) of nine hundred (900) views, corresponding to the 225° second range of source angles. Again, these numerical values are merely illustrative, and not meant to be exhaustive.

FIGS. 2A and 2B illustrate operation of the CT system to identify the range of source angles corresponding to short scan data to mitigate motion artifacts appearing in a computed tomography image of the heart 205. The motion artifacts mitigated may be the result of movement of the heart 205 that occurred during acquisition of a portion of the projection and backprojection data with the radiation source(s) 118 at source angles included in the extended scan data. The second range of source angles is to be identified to exclude at least a portion of the extended scan data that was acquired with the radiation source(s) 118 located at those source angles when the movement of the heart 205 occurred.

FIG. 2A is a schematic representation of the emission of parallel rays of radiation 120 at different angular locations within a range of source angles. The range of source angles over which the scan data is collected extends between R1 and R2, which is 225° about the axis of rotation 115 in FIG. 2A. A 225° range of source angles is sufficient to cause the set of parallel rays of radiation 120 emitted by the radiation source 118 to capture projection and backprojection data for the depth of the heart 205 along the center view 215, which is taken at the center angle β of the range R1-R2. Because parallel rays of radiation 120 are generally linear and orthogonal to the radiation source(s) 118 and the detector array 106, the relative alignment of the projections and backprojections for a stationary heart 205 at complementary angles should match (e.g., the data acquired at 90° and at 270° should match). Any differences or mismatches between the projections and backprojections is attributed to movement of the heart 205 during acquisition of the projection and backprojection data.

FIG. 2B is a schematic representation the acquisition of extended scan data and an identified range of view angles for short scan data of the specific example outlined above. As shown, the extended scan data was collected for a full scan, over a first range of source angles extending 360° about the axis of rotation 115. The first range of source angles for the extended scan data is represented by E1-E2 in FIG. 2B. The 960 views of the heart 205 are taken at equal intervals over this first range of source angles.

The computed tomography image is to be reconstructed from 600 views in the present example, which corresponds to a second range of source angles of 225° for the short scan data. Thus, the views in 225° of the full 360° full scan are to be used for reconstruction of the computed tomography image. As a result, the possible locations of the center view 210 (indicated by dashed lines) for the second range of source angles for the short scan data is between S1-S2. S1 is located 112.5° (225÷2) counterclockwise from the top center (0°) of the first range of source angles and S2 is located 112.5° (225÷2) clockwise from the top center (0°) of the first range of source angles. At each limit S1-S2 of the second range of source angles, the parallel rays of radiation 120 emitted perpendicular to the center view 210 capture projection and backprojection data for the full depth of the heart along the direction of the center view 210.

To determine the second range of source angles corresponding to short scan data that will mitigate motion artifacts in the reconstructed computed tomography image, the projections and the backprojections are compared to each other. Differences between the projection and the backprojection for the parallel rays of radiation 120 at each of the angular locations are indicative of movement of the heart 205 during the acquisition of the projection and the backprojection at the respective angular locations. If the projections and the backprojections for a view match, the heart 205 is considered to be stationary at that view.

Figure 3A:
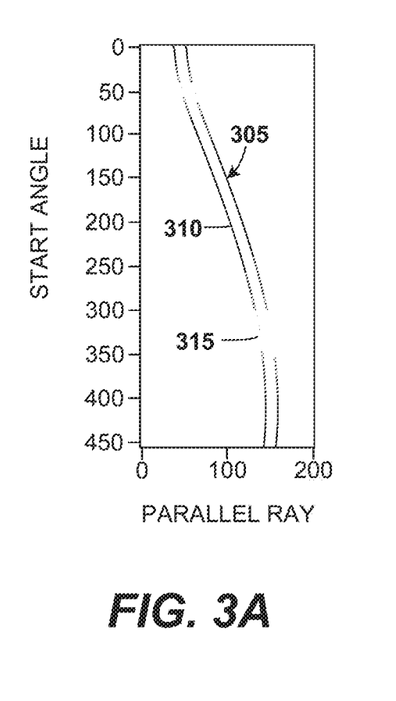
FIG. 3A is an illustrative embodiment of a motion map graphically depicting movement of a heart captured by scan data using parallel rays at different source angles.
Figure 3B:
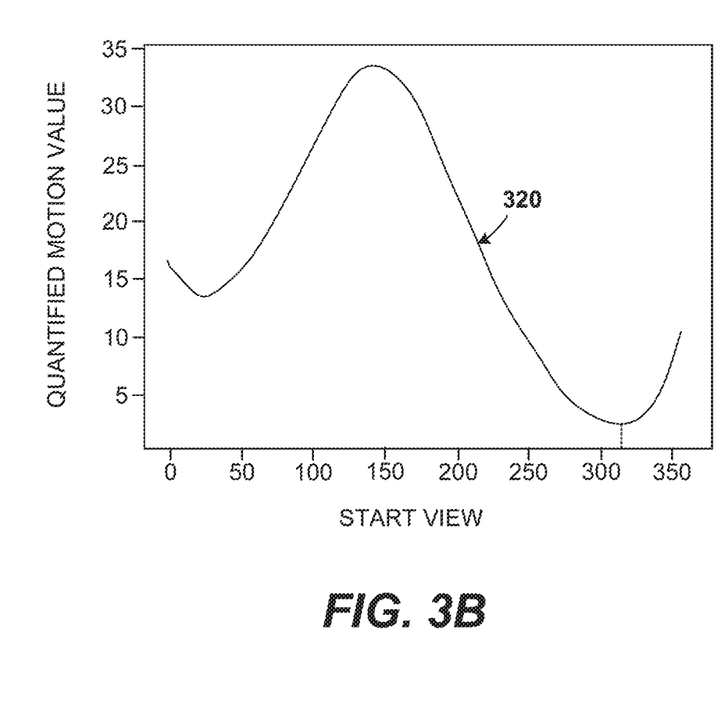
FIG. 3B is an illustrative embodiment of a motion curve graphically depicting a relationship between quantified movement of a heart and different start views of short scan data.

The motion of the heart 205 is quantified for each view based on the identified differences between the projections and the backprojections for the view. Quantification of the heart motion is based on the comparisons of the projections and backprojections. Thus, the heart motion is being quantified in the two-dimensional sinogram space, before the computed tomography image based on the acquired scan data is reconstructed. In other words, the heart motion captured by the extended scan data can be quantified without necessarily reconstructing the computed tomography image. The number of parallel rays p is a free parameter, and can be set to any desired value. In the present example, 200 parallel rays are utilized. For the set of parallel rays at each view (p, θ=β) for β=0-360° or for β=0-180°, the following can be determined, for each parallel ray, according to equations [1]-[3]:

$$\gamma = \arcsin\left(\frac{p}{R}\right) \quad [1]$$

$$\beta_{C1} = \theta - \gamma - \frac{\pi}{2} \quad [2]$$

$$\beta_{C2} = \theta + \gamma + \frac{\pi}{2} \quad [3]$$

where γ is the fan angle shown in FIG. 1, β is the gantry angle at the respective view as shown in FIG. 1, p is the parallel ray number, θ is the short scan center angle, and R is a distance separating the radiation source(s) 118 and the isocenter of the CT system, which is also shown in FIG. 1. This quantifying data can be represented graphically in a motion map and a motion curve, which are shown in FIG. 3A and FIG. 3B, respectively.

To generate the motion map, the difference between the projections and the backprojections along each of the parallel rays emitted perpendicular to the respective view position is determined according to equation [4]:

$$\text{MotionMap}(\theta,p) = (S(\beta_{C1},-\gamma) - S(\beta_{C2},\gamma))^2 \quad [4]$$

The result is a motion map shown in FIG. 3A. The ordinate of the motion map is the view numbers associated with the start angles for the first half of the scan. In the present example, 960 views make up the full 360° scan about the axis of rotation 115, and 480 views make up half a rotation about the axis of rotation 115. However, the relationships between the projection and the backprojection acquired for each view during the first half of the scan is expected to match the projection and the backprojection acquired for each view during the second half of the scan. Thus, the ordinate reflects the views between 0 and 480, representing start angles for one half of the full scan.

The abscissa of the motion map shown in FIG. 3A is the parallel ray number p. For clarity, only two curves 305, each representing differences between the projection and the backprojection along one of two different parallel rays, are shown in FIG. 3A. Those curves represent parallel ray numbers 150 and 160. However, as noted above, the present example utilizes 200 parallel rays so 200 of the curves 305 would appear in a complete motion map.

Each curve 305 in the motion map includes segments having different appearances. In FIG. 3A, the curves 305 include bold segments 310 and segments 315 that are barely visible. However, according to other embodiments, the curves 305 can include segments that are color coded, have different line weight, or can be provided with any other type of appearance. The variable appearance graphically differentiates between views corresponding to start angles that have different quantified levels of heart movement. Thus, in FIG. 3A, start angles adjacent to view 50 and start angles adjacent to view 335 exhibit lower levels of quantified movement based on the two parallel ray curves 305 shown.

FIG. 3B is a two-dimensional plot of quantified motion value versus start views of the second range of source angles for the short scan data. The curve 320 shows relative levels of heart motion captured within the scan data acquired in the second range of source angles, if the second rang were to start at various start angles. In FIG. 3B, the ordinate represents quantified motion values indicative of the average heart motion included in the scan data, and the abscissa represents the possible start views of the second range of source angles for the short scan data. There are 360 views that can be used as possible starting locations for the second range of source angles for the present example. Out of 960 total views, the computed tomography image is to be reconstructed from 600 views, leaving the 360 views to choose from.

The curve 320 in FIG. 3B is generated by averaging the quantified motion values over all parallel rays at each view, then average over sixty (60) angle positions around the center view as follows:

$$\text{tempMotion}(\theta) = \Sigma_p \text{MotionMap}(\theta,p) \quad [5]$$

$$\text{Motion}(\theta) = \text{Average}(\text{tempMotion}(\theta),60) \quad [6]$$

The resulting curve 320 represents a quantified amount of movement of the heart 205 that would appear in the reconstructed computed tomography image if the second range of source angles started at the various possible views. For the example shown in FIG. 3B, it appears a minimum exists in the curve 320 at the starting view of the bold segments 310. Accordingly, to minimize motion artifacts appearing in the computed tomography image, the short scan data can be selected as the subset of the extended scan data that was acquired beginning at the view of the bold segments 310. The short scan data includes the portion of the extended scan data acquired from the view of the bold segments 310 to view 909, which are the 600 views from which the computed tomography image is to be reconstructed.

The motion map and motion curve are graphical representations of the quantified movement of the heart as a function of view angles generated primarily for the benefit of the user 134 (FIG. 1), and for describing the present technology. However, embodiments of the present CT systems and methods can optionally identify the minimum quantified movement value through numerical analysis, without generating or displaying the motion map or motion curve in FIGS. 3A and 3B.

The short scan data is identified by comparing the quantified movement of the heart 205 in the two-dimensional scan data acquired at the different angular locations to a movement threshold. In the example above, the movement threshold was the quantified movement of the heart 205 at each of the possible views, and the lowest value of the quantified movement was selected. The view corresponding to the minimum quantified movement appearing in the motion curve of FIG. 3B was chosen as the start view, so the movement threshold in this example was the second lowest quantified motion value. However, according to other embodiments, the movement threshold may be a defined maximum value of quantified motion considered to be acceptable, a value within a defined relationship of the minimum value of the quantified motion, etc.

With the short scan data identified, the computed tomography image of the heart 205 can be reconstructed based, at least in part on the short scan data. The computed tomography image of the heart 205 can be reconstructed exclusively of a portion of the extended scan data that is not included in the short scan data. In other words, the computed tomography image can be reconstructed without the portion of the extended scan data acquired from views outside of the second range of source angles. According to other embodiments, the computed tomography image can be generated based, at least in part on the short scan data, optionally supplemented by a portion of the extended scan data acquired at views outside the second range of source angles.

Figure 4:
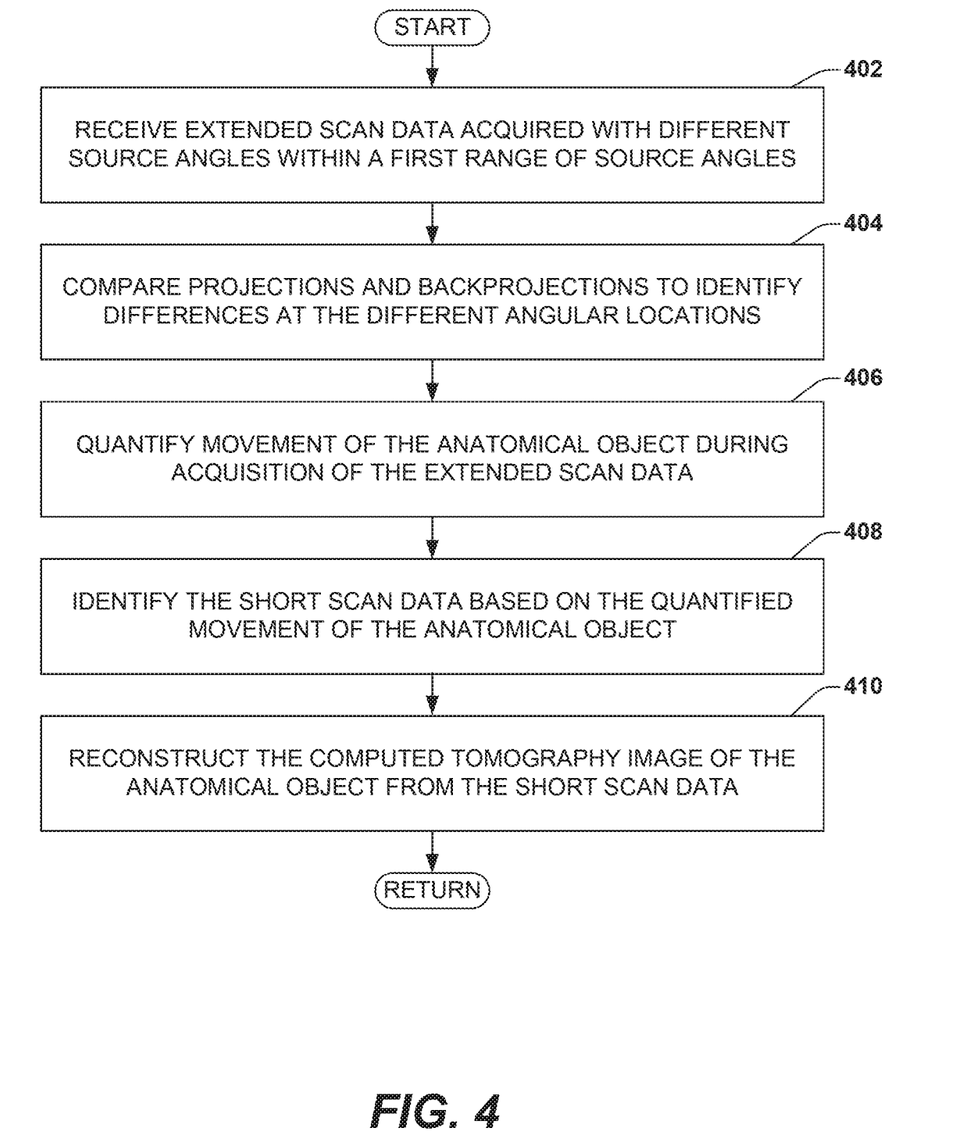
FIG. 4 illustrates a flow diagram of an illustrative method for mitigating motion artifacts in a computed tomography image.

FIG. 4 is a flow diagram schematically illustrating a method of detecting and mitigating motion artifacts in a computed tomography image of a heart based on two-dimension data. Extended scan data including projections and backprojections acquired for parallel rays emitted by a radiation source at different angular locations within a first range of source angles is received at step 402. The first range of source angles extends greater than 240° about an axis of rotation, and can exceed 270° about the axis of rotation, or be a full scan extending a complete 360° about the axis of rotation.

The projections and the backprojections acquired for each of the angular locations are compared to identify differences there between at step 404. Any such differences for an angular location are indicative of movement of the heart 205 during acquisition of the projections and the backprojections at that angular location.

Based on the differences identified between the projections and the backprojections, movement of the heart 205 during acquisition of the extended scan data at the different angular locations is quantified at step 406. Quantifying the movement of the heart 205 can be achieved numerically based on equations [1]-[3] above or utilizing any other model. The quantified movement values are indicative of the extent of any differences or mismatches between the projections and respective backprojections of the extended scan data.

The short scan data is identified at step 408. The short scan data includes a continuous subset of the extended scan data acquired with the radiation source 118 at different locations within a second range of source angles where the quantified movement of the heart 205 is a minimum, near minimum, or at least less than a movement threshold. The second range of source angles is less than the first range of source angles about the axis of rotation. For the above example, the first range of source angles is 360° about the axis of rotation 115, and the second range of the source angles is 225° about the axis of rotation 115, within the 360° of the first range of source angles.

The computed tomography image of the heart 205 is reconstructed from the short scan data at step 410. Reconstruction of the computed tomography image can be based, at least in part, on the short scan data. The computed tomography image may be reconstructed exclusively of the extended scan data that is not included in the short scan data. According to other embodiments, the computed tomography image can be reconstructed from a combination of the short scan data with a portion of the extended scan data acquired at view angles outside the second range of source angles.

Figure 5:
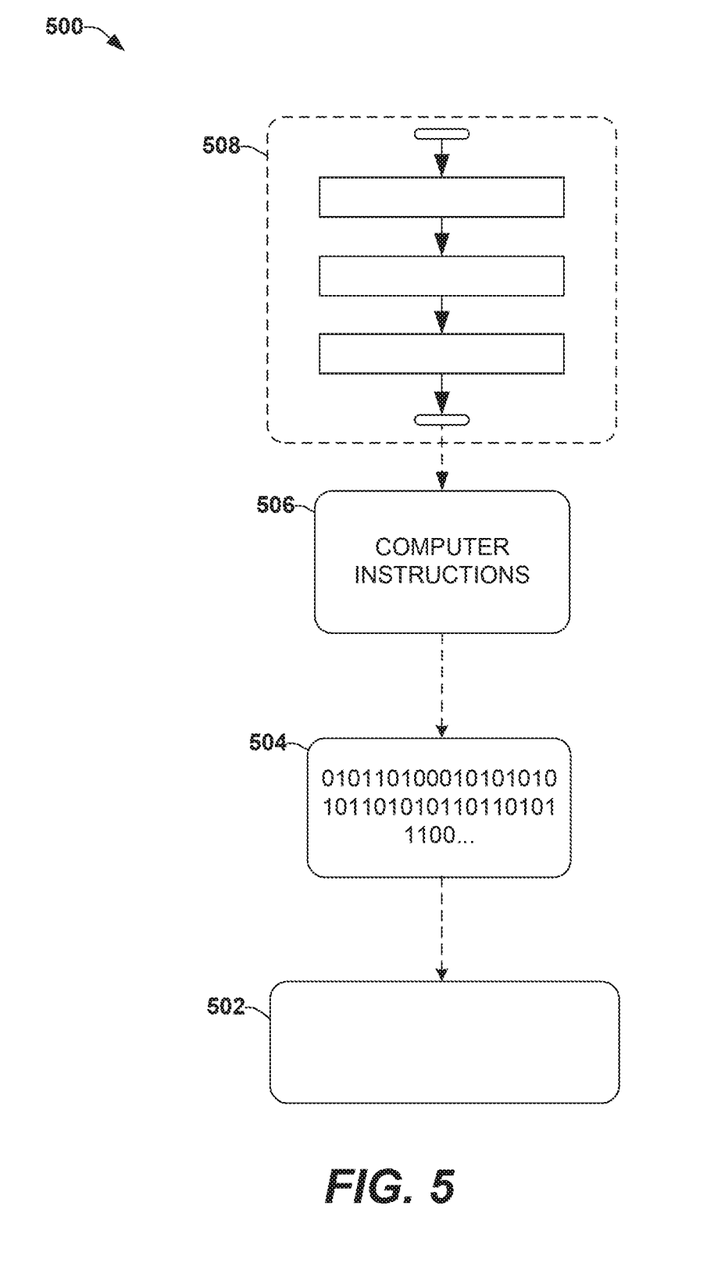
FIG. 5 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 5, wherein the implementation of embodiment 500 comprises a computer-readable medium 502 (e.g., a CD-R, DVD-R, or a platter of a hard disk drive), on which is encoded computer-readable data 504. This computer-readable data 504 in turn comprises a set of processor-executable instructions 506 configured to operate according to one or more of the principles set forth herein. In one such embodiment 500, the processor-executable instructions 506 may be configured to perform a method 508, such as at least some of the method depicted in FIG. 4. In another such embodiment, the processor-executable instructions 506 may be configured to implement a system, such as at least some of the example environment 100 of FIG. 1, for example. Many such computer-readable media may be devised by those of ordinary skill in the art that are configured to operate in accordance with one or more of the techniques presented herein.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing at least some of the claims.

As used in this application, the terms "component," "module," "system," "interface," and/or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Figure 6:
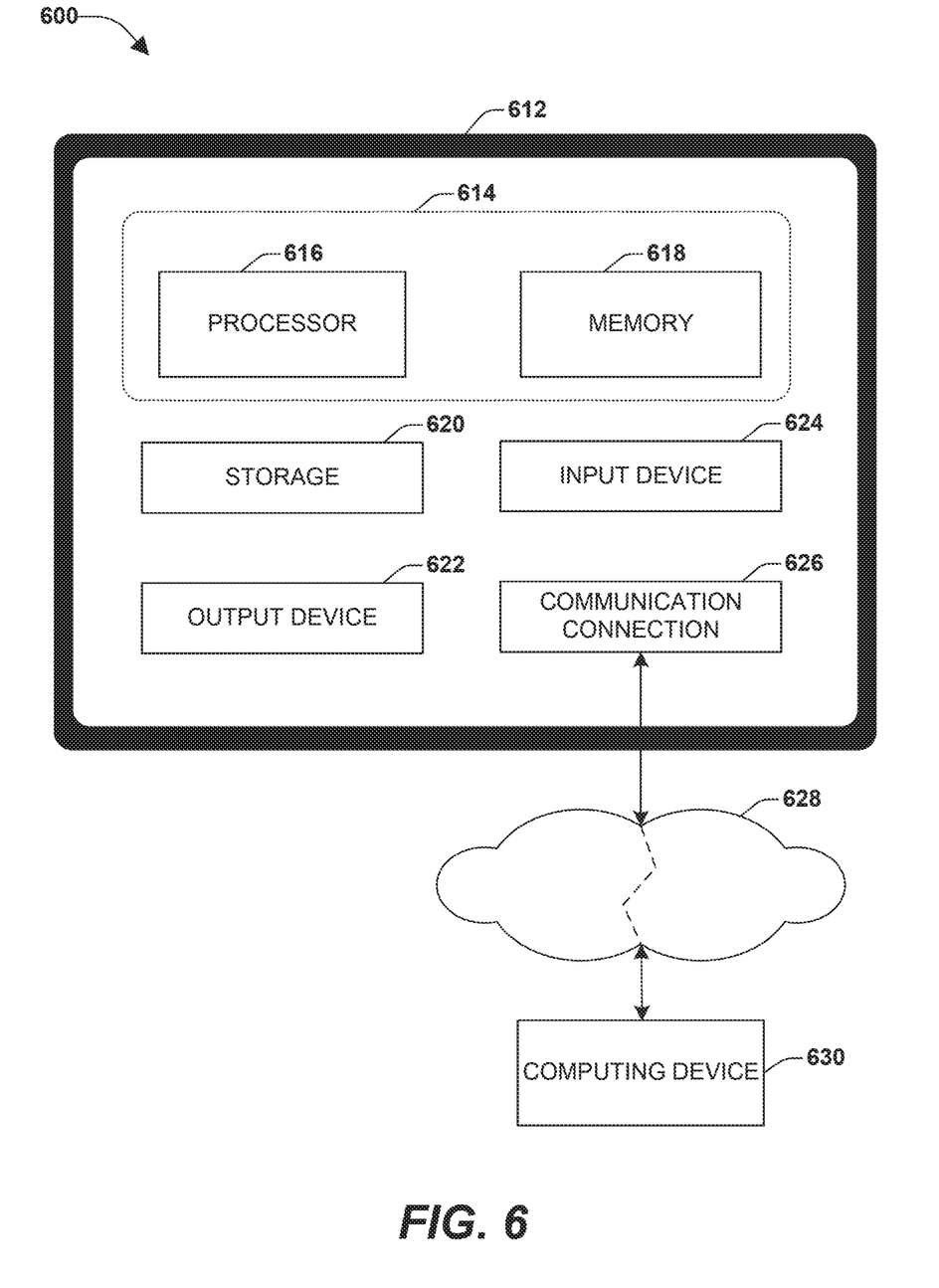
FIG. 6 illustrates an example computing environment wherein one or more of the provisions set forth herein may be implemented.

FIG. 6 and the following discussion provide a brief, general description of a suitable computing environment to implement embodiments of one or more of the provisions set forth herein. The operating environment of FIG. 6 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 6 illustrates an example of a system 600 comprising a computing device 612 configured to implement one or more embodiments provided herein. In one configuration, computing device 612 includes at least one processor 616 and memory 618. Depending on the exact configuration and type of computing device, memory 618 may be volatile (such as RAM, for example), non-volatile (such as ROM, flash memory, etc., for example) or some combination of the two. This configuration 614 is illustrated in FIG. 6 by dashed line.

In other embodiments, computing device 612 may include additional features and/or functionality. For example, computing device 612 may also include additional storage (e.g., removable and/or non-removable) including, but not limited to, magnetic storage, optical storage, and the like. Such additional storage is illustrated in FIG. 6 by storage 620. In one embodiment, computer readable instructions to implement one or more embodiments provided herein may be in storage 620. Storage 620 may also store other computer readable instructions to implement an operating system, an application program, and the like. Computer readable instructions may be loaded in memory 618 for execution by processor 616, for example.

The term "computer readable media" as used herein includes computer storage media. Computer storage media includes volatile and nonvolatile, removable and non-removable media implemented in any method or technology for storage of information such as computer readable instructions or other data. Memory 618 and storage 620 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by computing device 612. Computer storage media does not, however, include propagated signals. Rather, computer storage media excludes propagated signals. Any such computer storage media may be part of computing device 612.

Computing device 612 may also include communication connection 626 that allows computing device 612 to communicate with other devices. Communication connection 626 may include, but is not limited to, a modem, a Network Interface Card (NIC), an integrated network interface, a radio frequency transmitter/receiver, an infrared port, a USB connection, or other interfaces for connecting computing device 612 to other computing devices. Communication connection 626 may include a wired connection or a wireless connection. Communication connection 626 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Computing device 612 may include input device 624 such as keyboard, mouse, pen, voice input device, touch input device, infrared cameras, video input devices, and/or any other input device. Output device 622 such as one or more displays, speakers, printers, and/or any other output device may also be included in computing device 612. Input device 624 and output device 622 may be connected to computing device 612 via a wired connection, wireless connection, or any combination thereof. In one embodiment, an input device or an output device from another computing device may be used as input device 624 or output device 622 for computing device 612.

Components of computing device 612 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 612 may be interconnected by a network. For example, memory 618 may be comprised of multiple physical memory units located in different physical locations interconnected by a network.

Those skilled in the art will realize that storage devices utilized to store computer readable instructions may be distributed across a network. For example, a computing device 630 accessible via a network 628 may store computer readable instructions to implement one or more embodiments provided herein. Computing device 612 may access computing device 630 and download a part or all of the computer readable instructions for execution. Alternatively, computing device 612 may download pieces of the computer readable instructions, as needed, or some instructions may be executed at computing device 612 and some at computing device 630.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein. Also, it will be understood that not all operations are necessary in some embodiments.

Further, unless specified otherwise, "first," "second," and/or the like are not intended to imply a temporal aspect, a spatial aspect, an ordering, etc. Rather, such terms are merely used as identifiers, names, etc., for features, elements, items, etc. For example, a first object and a second object generally correspond to object A and object B or two different or two identical objects or the same object.

It may be appreciated that "example" and/or "exemplary" are used herein to mean serving as an example, instance, or illustration. Any aspect, design, etc., described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes," "having," "has," "with," or variants thereof are used in either the detailed description or the claims, such terms are intended to be inclusive in a manner similar to the term "comprising."

What is claimed is:

1. A method of mitigating motion artifacts in a computed tomography image of an anatomical object, the method comprising:
   receiving, at an image reconstructor, extended scan data comprising projections and backprojections acquired for parallel rays emitted by a radiation source at different angular locations within a first range of source angles, wherein the first range of source angles extends greater than 240° about an axis of rotation;
   comparing the projections and the backprojections to identify differences between the projections and the backprojections at the different angular locations;
   based on the identified differences between the projections and the backprojections, quantifying movement of the anatomical object during acquisition of the extended scan data at the different angular locations;
   identifying short scan data comprising a subset of the extended scan data acquired at different locations within a second range of source angles where the quantified movement of the anatomical object is less than a movement threshold, wherein the second range of source angles is less than the first range of source angles about the axis of rotation; and
   reconstructing the computed tomography image of the anatomical object from the short scan data.

2. The method of claim 1, wherein comparing the projections and the backprojections comprises conducting a comparison of the projections and the backprojections in a sinogram domain, before the computed tomography image is reconstructed.

3. The method of claim 1, wherein the computed tomography image of the anatomical object is reconstructed exclusive of a portion of the extended scan data that is not included in the short scan data.

4. The method of claim 1, wherein the first range of source angles extends at least 270° about the axis of rotation.

5. The method of claim 4, wherein the first range of source angles extends 360° about the axis of rotation.

6. The method of claim 5, wherein the second range of source angles extends up to 240° about the axis of rotation.

7. The method of claim 1 comprising:
   determining the movement threshold based on the quantified movement of the anatomical object during acquisition of the extended scan data at the different angular locations within the first range of source angles.

8. The method of claim 1, wherein the extended scan data corresponds to a midplane sinogram captured by one or more centrally-located sensors in a detector array.

9. A computed tomography system, comprising:
   a radiation source;
   a detector array; and
   an image reconstructor configured to:
      receive extended scan data comprising projections and backprojections acquired for parallel rays emitted by the radiation source at different angular locations within a first range of source angles, wherein the first range of source angles extends greater than 240° about an axis of rotation of the radiation source;
      compare the projections and the backprojections to identify differences between the projections and the backprojections at the different angular locations;
      based on the identified differences between the projections and the backprojections, quantify movement of an anatomical object during acquisition of the extended scan data at the different angular locations;

identify short scan data comprising a subset of the extended scan data acquired at different locations within a second range of source angles where the quantified movement of the anatomical object is less than a movement threshold, wherein the second range of source angles is less than the first range of source angles about the axis of rotation; and reconstruct a computed tomography image of the anatomical object from the short scan data.

10. The computed tomography system of claim 9, wherein the image reconstructor is configured to compare the projections and the backprojections in a sinogram domain, before the computed tomography image is reconstructed.

11. The computed tomography system of claim 9, wherein the image reconstructor is configured to reconstruct the computed tomography image of the anatomical object exclusive of a portion of the extended scan data that is not included in the short scan data.

12. The computed tomography system of claim 9, wherein the first range of source angles extends at least 270° about the axis of rotation.

13. The computed tomography system of claim 12, wherein the first range of source angles extends 360° about the axis of rotation.

14. The computed tomography system of claim 13, wherein the second range of source angles extends up to 240° about the axis of rotation.

15. The computed tomography system of claim 9 comprising:

determining the movement threshold based on the quantified movement of the anatomical object during acquisition of the extended scan data at the different angular locations within the first range of source angles.

16. The computed tomography system of claim 9, wherein the extended scan data corresponds to a midplane sinogram captured by one or more centrally-located sensors in a detector array.

17. A non-transitory computer readable medium comprising computer executable instructions that when executed via a processing unit cause performance of operations involving extended scan data comprising projections and backprojections acquired for parallel rays emitted by a radiation source at different angular locations within a first range of source angles, wherein the first range of source angles extends greater than 240° about an axis of rotation, the operations comprising:

comparing the projections and the backprojections to identify differences between the projections and the backprojections at the different angular locations;

based on the identified differences between the projections and the backprojections, quantifying movement of an anatomical object during acquisition of the extended scan data at the different angular locations;

identifying short scan data comprising a subset of the extended scan data acquired at different locations within a second range of source angles where the quantified movement of the anatomical object is less than a movement threshold, wherein the second range of source angles is less than the first range of source angles about the axis of rotation; and reconstructing a computed tomography image of the anatomical object from the short scan data.

18. The non-transitory computer readable medium of claim 17, wherein the projections and the backprojections are compared in a sinogram domain, before the computed tomography image is reconstructed.

19. The non-transitory computer readable medium of claim 17, wherein the computed tomography image of the anatomical object is reconstructed exclusive of a portion of the extended scan data that is not included in the short scan data.

20. The non-transitory computer readable medium of claim 17, wherein the operations comprise:

determining the movement threshold based on the quantified movement of the anatomical object during acquisition of the extended scan data at the different angular locations within the first range of source angles.

* * * * *